US010219755B2

United States Patent
Kun et al.

(10) Patent No.: US 10,219,755 B2
(45) Date of Patent: Mar. 5, 2019

(54) NONINVASIVE MEASUREMENT OF ANALYTE CONCENTRATION USING METHODS AND SYSTEMS OF POST-BALANCING

(71) Applicant: VALOA TECHNOLOGIES, INC., Holden, MA (US)

(72) Inventors: Stevan Kun, Worcester, MA (US); Hannu Harjunmaa, Holden, MA (US); Rebecca Burrell, Rowley, MA (US)

( * ) Notice: Subject to any disclaimer, the term of this patent is extended or adjusted under 35 U.S.C. 154(b) by 0 days.

(21) Appl. No.: 15/604,622

(22) Filed: May 24, 2017

(65) Prior Publication Data

US 2018/0070884 A1 Mar. 15, 2018

Related U.S. Application Data

(63) Continuation of application No. 14/601,395, filed on Jan. 21, 2015, now abandoned.

(51) Int. Cl.
*A61B 5/1455* (2006.01)
*A61B 5/00* (2006.01)
(Continued)

(52) U.S. Cl.
CPC ........ *A61B 5/7246* (2013.01); *A61B 5/14532* (2013.01); *A61B 5/14546* (2013.01);
(Continued)

(58) Field of Classification Search
CPC .............. A61B 5/1455; A61B 5/14532; A61B 5/14546; A61B 5/1451; A61B 5/7246; A61B 2562/0238
See application file for complete search history.

(56) References Cited

U.S. PATENT DOCUMENTS 3,638,640 A * 2/1972 Shaw ................. A61B 5/14552
600/323
5,099,123 A * 3/1992 Harjunmaa ........ A61B 5/14532
600/310

(Continued)

*Primary Examiner* — Eric F Winakur
(74) *Attorney, Agent, or Firm* — Gerry A. Blodgett; David A. Blodgett; Blodgett & Blodgett, P.C.

(57) ABSTRACT

A noninvasive method for estimating a concentration of a target analyte in a sample comprises generating a first and second (reference) radiation, a principal radiation and a target analyte carrier detection radiation; directing the first, second, principal and the target analyte carrier detection radiations at the sample which includes the target analyte; and detecting a first, second, principal and target analyte carrier detection amount of the radiation that leaves the sample. The method further comprises modulating the sample thickness in order to achieve time-wise or spatial target analyte concentration variation within the sample. The method further comprises generating first, second, principal and target analyte carrier detection measurement data based respectively on the first, second, the principal and the target analyte carrier detected amounts of radiation; numerically processing the first, second, principal and target analyte carrier detection measurement data to obtain a weighted combination of the first measurement data and the second measurement data that balances the principal measurement data with respect to a sample background; and estimating the concentration of the target analyte based on the difference between the balanced weighted combination of the first measurement data and the second measurement data vs. the principal measurement data.

30 Claims, 4 Drawing Sheets

(51) Int. Cl.
    *A61B 5/145*    (2006.01)
    *A61B 5/024*    (2006.01)
(52) U.S. Cl.
    CPC ...... *A61B 5/14552* (2013.01); *A61B 5/02422* (2013.01); *A61B 2562/0238* (2013.01)

(56) References Cited

U.S. PATENT DOCUMENTS

| | | | | |
|---|---|---|---|---|
| 5,112,124 | A | * | 5/1992 | Harjunmaa ........ A61B 5/14532 600/316 |
| 5,137,023 | A | * | 8/1992 | Mendelson ........ A61B 5/14532 600/316 |
| 5,178,142 | A | * | 1/1993 | Harjunmaa ........ A61B 5/14532 600/316 |
| 5,720,284 | A | * | 2/1998 | Aoyagi ............. A61B 5/14551 600/322 |
| 6,223,063 | B1 | * | 4/2001 | Chaiken ............ A61B 5/14532 600/310 |
| 8,126,527 | B2 | * | 2/2012 | Marcinek ............ A61B 5/1455 600/322 |
| 8,406,838 | B2 | * | 3/2013 | Kato ................. A61B 5/14553 600/322 |

\* cited by examiner

NONINVASIVE MEASUREMENT OF ANALYTE CONCENTRATION USING METHODS AND SYSTEMS OF POST-BALANCING

The present disclosure generally relates to the field of biomedical testing. More specifically, the present disclosure relates to methods and apparatus for noninvasive measurement of the concentration of target analytes in body tissues.

BACKGROUND OF THE INVENTION

Noninvasive diagnosis and measurement of blood glucose concentration has attracted tremendous attention in the past two decades because of the emergence of diabetes as a public health epidemic. In current practice, all available portable end-user devices for measuring blood glucose require puncturing of the fingertip to obtain a blood sample. The blood sample is then placed on a test strip that is read by a meter to indicate the glucose concentration. These devices are very compact and reasonably accurate, but puncturing the fingertip to obtain a blood sample is inconvenient, painful, and poses a risk of infection. For users who are elderly or vision-impaired, these smaller devices may also be difficult to use. In addition, the cost of systematic and continuous use of single-use test strips is high. Noninvasive devices for accurately measuring blood glucose may address the above listed limitations of invasive glucose measurement devices, but are not commercially available at present.

Noninvasive measurement of glucose offers the potential for increased frequency of testing and more responsive control of blood glucose concentrations through concomitant adjustment of insulin doses. Noninvasive detection techniques also offer the potential for accurate, portable, closed-loop systems for monitoring and regulating insulin dosage without an indwelling sensor. These prospective advantages have led to considerable interest in the commercialization of noninvasive glucose monitoring devices.

One of the possible methods of performing noninvasive glucose measurements includes measuring tissue attenuation of light radiation in the near infrared energy spectrum (approximately 650 nm to 2700 nm). U.S. Pat. No. 5,099,123 to Harjunmaa et al. (the '123 patent), which is incorporated herein in its entirety by reference, discloses a balanced differential (or OPTICAL BRIDGE™) method for measurement of a target analyte concentration (e.g. glucose concentration) in a sample background matrix (e.g. body fluids and tissue) of a sample (e.g. an earlobe). To obtain measurement data, the method utilizes two wavelengths: a principal wavelength, which is absorbed by the target analyte, and a reference wavelength, which is less absorbed by the target analyte, that is before the measurement selected (i.e. fine tuned from its nominal or initial value) by the OPTICAL BRIDGE™ balancing process. The OPTICAL BRIDGE™ balancing process includes adjusting the reference wavelength so that the sample background is differentially (between the principal and reference wavelengths) "invisible". By making the sample background differentially invisible, any difference between the principal wavelength and the reference wavelength measurement data can be attributed to an amount of target analyte in the sample.

Subsequently, in U.S. Pat. No. 5,178,142, which is incorporated herein by reference, Harjunmaa et al. disclosed a method of changing the extracellular to intracellular fluid ratio of the tissue matrix by varying the mechanical pressure on the tissue, and performing the OPTICAL BRIDGE™ balancing when there is a minimum level of analyte present in the sample.

In U.S. Pat. No. 7,003,337, which is incorporated herein by reference, Harjunmaa et al. disclosed continuous estimation of the volume of sample fluid (e.g. blood) containing the target analyte (e.g. glucose) within the sample (e.g., earlobe) using another radiation (e.g. green light which is absorbed by hemoglobin). The fluid volume estimation is combined with the measurement data corresponding to the principal and reference wavelengths to provide for an improved calculation of the analyte concentration. Further, in U.S. Pat. No. 8,175,666 (the '666 patent), which is also incorporated herein by reference, Harjunmaa et al. disclosed a method of producing a radiation beam using three fixed-wavelength diode lasers, wherein varying the relative intensities of the two fixed-wavelength reference diode lasers produces an effect comparable to tuning (i.e. varying) of the reference wavelength.

Other related patents include U.S. Pat. Nos. 5,112,124; 5,137,023; 5,183,042; 5,277,181 and 5,372,135, each of which is incorporated by reference herein in its entirety. Related patent applications include U.S. patent application Ser. Nos. 13/835,143 and 13/441,467, each of which is incorporated by reference herein in its entirety.

SUMMARY OF THE INVENTION

In this application, in accordance with the '123 patent, we are referring to the principal wavelength as one that is significantly absorbed by the target analyte. In accordance with the '123 and '666 patents, we are referring to the reference wavelengths as those less absorbed by the target analyte; their nominal (initial) wavelengths are selected based on the selected principal wavelength and expected optical characteristics of the samples (may be fixed by the instrument design). We will refer to the Target Analyte Carrier Indicator as a noninvasively obtained measure of the amount of substance in which the target analyte is dissolved or diluted in within the sample (if applicable). More specifically, if the Target Analyte Carrier is blood, we are referring to the Blood Indicator as a noninvasively obtained measure of the amount of blood in the sample. As indicated in U.S. Pat. No. 7,003,337 the Blood Indicator may be a recording of green light (highly absorbed by blood) probing the sample. In addition, the Target Analyte Carrier Indicator may be obtained by other methods, including, but not limited to: laser speckle contrast imaging, infrared thermal imaging, laser Doppler, ultrasound Doppler, impedance spectroscopy/imaging. Also, in this application, we are referring to the sample background as all components of the sample that do not contain the target analyte or the target analyte carrier. In this application, we are referring to auxiliary data as recordings of constants or time-varying signals during the measurement that are not of optical nature (e.g. temperature, sample thickness, sample pressure, signal gains, etc.).

In the patents referenced in the Background section of this application, all methods that refer to the OPTICAL BRIDGE™ balancing are optical in nature: during the balancing procedure that precedes the data collection, first the reference wavelength is determined, then the intensities and/or wavelengths of the (reference) light sources are set to generate the equivalent reference wavelength that will be used throughout the measurement. We will call this optical OPTICAL BRIDGE™ balancing, or OOBB. The measurement that includes data collection and signal processing is performed afterwards. If the balancing is done suboptimally, the accuracy of the measurement is comprised.

In this application, we are disclosing a method of so called Post-Balancing of the OPTICAL BRIDGE™, which involves data acquisition and a numerical OPTICAL BRIDGE™ balancing method that is applied to the collected data. Post-Balancing may be used in conjunction with the optical balancing methods outlined in the patents referenced in the Background section. However, in general, Post-Balancing may be used on signals acquired from any set of light sources.

In general, the Post-Balancing process can be broken down into the following three steps: 1) the measurement, that involves data acquisition of time varying signals produced by illumination of the sample with light sources of one or more wavelengths, data acquisition of the target analyte carrier indicator signal, and other auxiliary signals that represent sample or measurement system parameters (e.g. thickness, pressure, temperature, wavelengths, etc.); 2) numerical processing of the acquired data to calculate parameters (e.g. weights, attenuation coefficients, etc.) needed to produce the OPTICAL BRIDGE™ signals that are sensitive to the variation of the amount of the target analyte or target analyte carrier in the sample (and are insensitive to the variation of the amount of the sample background that does not contain the target analyte); 3) target analyte concentration calculation. While optical balancing is a "one size fits all" method because it is performed before the measurement is performed and data could be analyzed, a distinctive advantage of Post-Balancing is that it is done after the measurement data is acquired and analyzed, therefore, it can be tuned to each measurement, and iterated until the required balancing criteria are reached.

An exemplary noninvasive method for estimating a concentration of a target analyte in a sample may include generating a first reference radiation having a first reference wavelength, a second reference radiation having a second reference wavelength, a principal radiation having a principal wavelength, and a target analyte carrier indicator radiation, using a first reference light source, a second reference light source, a principal light source, and a target analyte carrier indicator light source, respectively. The method may also include directing the first reference radiation, the second reference radiation, the principal radiation, and the target analyte carrier indicator radiation at the sample which includes the target analyte. The method may further include detecting, with one or more detectors, a first amount of the first reference radiation, a second amount of the second reference radiation, a third amount of the principal radiation, and a fourth amount of the target analyte carrier indicator radiation that leaves the sample. The method may include a time-wise and/or spatial variation of the background thickness of the sample. The method may include time-wise and/or spatial variation of the target analyte contents in the sample. The method may also include generating first reference measurement data, second reference measurement data, principal measurement data, and target analyte carrier indicator measurement data, based respectively on the first amount, the second amount, the third amount, and the fourth amount that are detected. The method may also include generating auxiliary data. The method may further include processing the first reference measurement data, second reference measurement data, principal measurement data, the target analyte carrier indicator data, and the auxiliary data, to obtain a weighted combination of the first reference measurement data and the second reference measurement data that balances the principal measurement data with respect to a sample background—this is referenced as the Combined Bridge signal. The method may also include estimating the concentration of the target analyte based on the Combined Bridge signals.

An exemplary noninvasive apparatus for estimating a concentration of a target analyte in a sample may include a first reference light source for generating a first reference radiation, and a second reference light source for generating a second reference radiation. The apparatus may also include a principal light source for generating a principal radiation. The apparatus may also include a target analyte carrier detection light source for generating a target analyte carrier detection radiation. The apparatus may include circuitry for enabling variation of wavelengths and intensities of the light sources. The apparatus may further include one or more detectors for detecting the first reference radiation, the second reference radiation, the principal radiation, and the target analyte carrier detection radiation, and generating corresponding first reference measurement data, second reference measurement data, principal measurement data and target analyte carrier detection measurement data. The apparatus may further include modules for generating and one or more detectors capable of detecting the auxiliary data (e.g. pressure, sample thickness, sample temperature). The apparatus may include a mechanism for time-wise and/or spatial variation of the target analyte, target analyte carrier and/or background content within the sample. The apparatus may also include a controller system (including, but not limited to processor, memory, I/O, display) configured to process the first reference measurement data, second reference measurement data, principal measurement data, the target analyte carrier detection data and auxiliary data, using one or more processors (e.g. microprocessors) or customized signal or data processing components (e.g. ASICs), to generate the Combined Bridge signals. The controller may also be used to estimate the concentration of the target analyte based on the Combined Bridge signals.

It is to be understood that both the foregoing general description and the following detailed description are exemplary and explanatory only and are not restrictive of the invention, as claimed.

BRIEF DESCRIPTION OF DRAWINGS

The accompanying drawings, which are incorporated in and constitute a part of this specification, illustrate embodiments of the invention and together with the description, serve to explain the principles of the various aspects of the invention.

DETAILED DESCRIPTION

Reference will now be made in detail to embodiments consistent with the present disclosure, examples of which are illustrated in the accompanying drawings.

Figure 1:
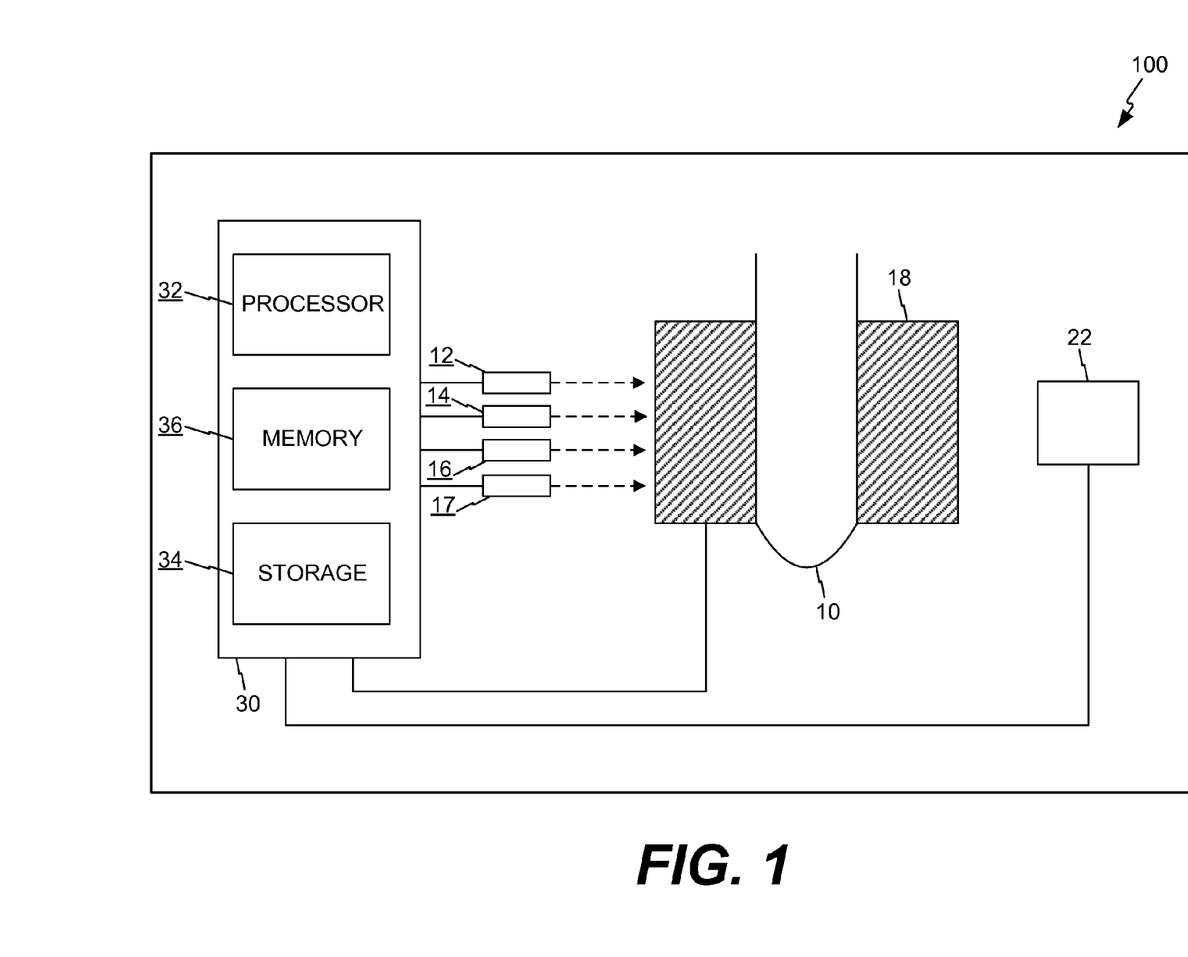
FIG. 1 depicts an exemplary noninvasive analyte measurement apparatus according to an embodiment of the present disclosure.

FIG. 1 depicts an exemplary analyte measurement device 100 for noninvasive measurement of a concentration of a target analyte in a sample 10. Sample 10 may be, for example, a human body part, such as part of an earlobe or a fingertip. In another example, sample 10 may be a part of an animal body or something other than a biological specimen. The target analyte may be, for example, a component for which determining its concentration is desired, such as glucose present in human blood. The target analyte carrier may be a sample component in which the target analyte is dissolved or diluted. For example, it may be blood in which glucose is dissolved. In addition to the target analyte and target analyte carrier, sample 10 may also include sample background which comprises other components of sample 10 that do not contain or are not the target analyte. In the example of an earlobe or finger sample, in which the target analyte is glucose and the target analyte carrier is blood, the sample background may be all other tissue components than glucose and blood (e.g. cellular tissue, interstitial fluid, fat, proteins, etc.).

Analyte measurement device 100 may include two (or more) reference light sources 12, 14, one (or more) principal light source 16, a target analyte carrier indicator (e.g. green) light source 17, a sample content (time-wise and/or spatial) alteration device 18, a signal detector 22, and a controller 30, which are used to obtain measurements of the target analyte and estimate the concentration of the target analyte. In practice, it should be understood that the detector 22 could take the form of one detector or a plurality of detectors.

The target analyte, and/or target analyte carrier, and/or background content alteration device 18, which may be in contact with the sample, may contain auxiliary data recording components (e.g. force transducer, linear encoder, thermometer).

Light source 12 may be used to generate a lower reference wavelength ($\lambda_L$) radiation and light source 14 may be used to generate a higher reference wavelength ($\lambda_H$) radiation respectively, which are directed at sample 10. In this text, subscript "L" indicates lower reference, "H" indicates higher reference, and "P" indicates principal. In the example of blood glucose as the target analyte, $\lambda_L$ and $\lambda_H$ may be different wavelengths in the near infrared or infrared range. Exemplarily, the light sources may be diode lasers. Exemplarily, $\lambda_L$ and $\lambda_H$ may be in the range of 650 nm to 2700 nm, specifically between 1300 nm and 1450 nm, and more specifically around 1380 nm. For example, $\lambda_L$ may be about 1375 nm and $\lambda_H$ may be about 1385 nm. In an alternative embodiment, LEDs or other known electromagnetic radiation sources may be used as light source 12 and/or light source 14. In another embodiment, multiple radiation sources may be used to generate the reference wavelengths.

Light source 16 may emit electromagnetic radiation of wavelength $\lambda_P$, which is the principal wavelength. $\lambda_P$ may be a different wavelength from $\lambda_L$ and $\lambda_H$, and specifically may be a wavelength at which the target analyte has a greater attenuation coefficient as compared with $\lambda_L$ and $\lambda_H$. In the case in which the target analyte is glucose, $\lambda_P$ may be a different wavelength from $\lambda_L$ and $\lambda_H$ in the near-infrared or infrared range. Exemplarily, the light source may be a diode laser. $\lambda_P$ may be exemplarily in the range of 650 nm to 2700 nm, more specifically between 1450 nm and 1650 nm, or around 1630 nm. In another embodiment, $\lambda_P$ may be generated by more than one diode laser, or by one or more LEDs or other known electromagnetic sources or their combinations.

Light sources 12, 14, and 16 may be directed to emit their radiations of wavelengths $\lambda_L$, $\lambda_H$, and $\lambda_P$ at a measurement site of sample 10 containing the target analyte within a sample. The measurement site is the specific part of sample 10 within which the $\lambda_L$, $\lambda_H$, and $\lambda_P$ radiations are interacting with sample 10 and the analyte concentration is being measured. The $\lambda_L$, $\lambda_H$, and $\lambda_P$ electromagnetic radiations may arrive at sample 10, and portions of the radiations may be attenuated by sample 10 (e.g. by the sample background and/or by the target analyte carrier, and/or by the target analyte). Portions of the radiations that are not attenuated by sample 10 may be transmitted through sample 10, or reflected by and/or transflected by sample 10. The amount of each radiation of wavelengths $\lambda_L$, $\lambda_H$, and $\lambda_P$ that is attenuated by sample 10 depends on the respective attenuation coefficients $\mu_{L\text{-}background}$, $\mu_{H\text{-}background}$, and $\mu_{P\text{-}background}$ of the sample background, the respective attenuation coefficients $\mu_{L\text{-}targetCarrier}$, $\mu_{H\text{-}targetCarrier}$, and $\mu_{P\text{-}targetCarrier}$ of the target analyte carrier (if any), and the respective attenuation coefficients $\mu_{L\text{-}target}$, $\mu_{H\text{-}target}$, and $\mu_{P\text{-}target}$ of the target analyte, at these wavelengths. An exemplary method of determining these attenuation coefficients is discussed in further detail below. In one embodiment, measurements of the intensity of the portions that are transmitted through sample 10 may be used to estimate the target analyte concentration within the sample or within the target analyte carrier. In another embodiment, measurements of the intensity of the portions that are reflected and/or transflected by sample 10 may be used to estimate the target analyte concentration within the sample or target analyte carrier. Embodiments are described in further detail below with respect to measuring the non-attenuated portions of the transmitted $\lambda_L$, $\lambda_H$, and $\lambda_P$ radiations. However, it is understood that the methods and systems described herein can be modified by a person of ordinary skill in the art to utilize measurements of the reflected and/or transflected portions of the $\lambda_L$, $\lambda_H$, and $\lambda_P$ radiations.

Target analyte carrier indicator light source 17 may emit a green-colored electromagnetic radiation $\lambda_G$, for example a radiation of a wavelength between about 500 nm and about 600 nm. For example, the $\lambda_G$ could be in a range between 510 and 540 nm. In an exemplary embodiment, target analyte carrier indicator light source 17 may be an LED that emits a green 525 nm wavelength radiation. Target analyte carrier indicator light source 17 may also be directed to emit its radiation at the measurement site of sample 10, and in an exemplary embodiment the green-colored wavelength $\lambda_G$ of LED 17 may be suitable for detection of the volume of blood in sample 10, because blood absorbs preferentially in the green wavelength range. That is, a relatively small increase or decrease in the amount of blood in sample 10 could change the amount of green radiation that is attenuated by sample 10 and the amount of green radiation that is measured by detector 22. In another embodiment, $\lambda_G$ may be generated by more than one diode laser, by more than one LED or other multiples or combinations of known electromagnetic sources.

In some embodiments as discussed in further detail below, the amount and/or spatial distribution of sample background and/or target analyte and/or target analyte carrier present within the measurement site of sample 10 may be varied by, for example, altering the total thickness of sample 10 using a sample content alteration device 18. The sample content alteration device 18 may be any device that can alter, for example, the thickness of sample 10 in a controllable way. For example, sample content alteration device 18 may be a device configured to compress sample 10 to various thicknesses. In the example of an earlobe or finger sample, sample content alteration device 18 may be configured to compress (and subsequently release) sample 10 such that displaceable target analyte carrier fluid, e.g., blood, is displaced from (and subsequently permitted to reflow into) the earlobe or finger sample. As a result, some amount of the glucose that resides in the blood may also be displaced from sample 10. In addition, compressing sample 10 may also displace some amount of the sample background from the measurement site. In an exemplary method described in further detail below, changing the amount of glucose and/or blood and/or the sample background in the measurement site may be used in the process to determine attenuation coefficients of blood and/or the sample background, as well as the concentration of glucose. The sample content alteration device 18 may be a clamping device, non-limiting examples of which include a clamp, a press, or a pressure cuff which squeezes and unsqueezes sample 10. In an exemplary embodiment, device 18 may contain a linear actuator moving the signal detector 22 against sample 10 with a sufficient force to squeeze sample 10 and alter its content.

In some embodiments as discussed in further detail below, the sample content alteration device 18, which may be in contact with the sample, may contain auxiliary data recording components. In an exemplary method, in which device 18 is a thickness alteration device, device 18 may also include a position encoder that may generate a signal proportional to the thickness of sample 10. In another exemplary embodiment, device 18 may also contain a force transducer that may generate a signal proportional to the force or pressure that is being applied to sample 10. In other exemplary embodiments, device 18 may also contain a thermometer that can measure the temperature of the sample.

Signal detector 22 may consist of one or more photodiodes or any other devices that detect electromagnetic radiation emitted by light sources 12, 14, 16, and/or 17 to the measurement site of sample 10 and not attenuated by sample 10. In one embodiment, one signal detector 22 may receive the four radiations $\lambda_L$, $\lambda_H$, $\lambda_P$, and $\lambda_G$. In another embodiment, each radiation or some of the radiations may be detected by different signal detectors 22, in some cases with a fixed or variable optical filter preceding one or more of the detectors 22. Signal detector 22 may detect the attenuated intensities of the radiations and output measurement signals based on the detected intensities. An exemplary signal detector 22 may be a silicon photodiode and/or an indium-gallium arsenide photodiode and/or a germanium photodiode. Another exemplary signal detector 22 may be a camera.

Controller 30 may include one or more computing processors 32, such as microprocessors or microcontrollers, which execute instructions stored on one or more memory storage devices 34, such as a flash drive, magnetic disk drive, CD-ROM, semiconductor ROM drive, etc. Controller 30 may also include memory 36, such as RAM or DRAM, used by processor 32 for executing the instructions. In another embodiment, all or part of processor 32, memory storage device 34, and/or memory 36 may be located in one or more devices that are physically separate from other parts of analyte measurement device 100, as one of ordinary skill in the art would appreciate. For example, part of processor 32, memory storage device 34, and/or memory 36 may be part of a separate computer device, with which controller 30 is in communication with via wired and/or wireless communication channels. Based on the instructions executed by processor 32, controller 30 may be configured to control the operation of light sources 12, 14, 16, and/or 17. For example, controller 30 may be configured to control the timing and/or power for driving light sources 12, 14, 16, and/or 17. For example, controller 30 may be configured to control the wavelengths of light sources 12, 14, 16, and/or 17. Based on the instructions executed by processor 32, controller 30 may also be configured to control the operation of the sample content alteration device 18 by, for example, controlling the thickness or pressure of sample 10 during acquisition of measurements.

In addition to controlling the operation of light sources 12, 14, 16, 17, and/or the sample content alteration device 18, controller 30 may be configured to receive the measurement signals output from signal detector 22. In addition, controller 30 may be configured to receive the auxiliary signals and/or data (e.g. pressure, sample thickness) produced by submodules of device 18. In addition, controller 30 may be configured to digitize all received analog signals into discrete readings—(i.e. measurement data). Readings that correspond to the same signal will be referred to as measurement data arrays. Processor 32 may process the measurement data to determine parameters that are used to adjust the operation of light sources 12, 14, 16, 17, and/or the sample content alteration device 18. Processor 32 may also process the measurement data to determine the analyte concentration within sample 10. In one embodiment, processing the measurement data to determine the analyte concentration may include performing Post-Balancing as described in further detail below. Storage device 34 may store the measurement data and/or the processed data, as well as instructions for processing the measurement data. Memory 36 may be used by processor 32 during processing of the measurement data. Exemplary methods of obtaining and processing measurement data are described in more detail below.

In one embodiment, instead of using software programmable processing devices like microprocessors, all or part of the processing of the measurement data within device 30 can be done by custom designed components, for example, ASICs (application specific integrated circuits).

Previously disclosed methods of measuring a concentration of a target analyte include a process of pre-adjusting the $\lambda_L$ and $\lambda_H$ radiations, before the acquisition of measurement data, by performing an optical method of OPTICAL BRIDGE™ balancing (OOBB) as, for example, disclosed in the '666 patent. Relative powers of $\lambda_L$ and $\lambda_H$ are set so that the physical combination of the $\lambda_L$ radiation and the $\lambda_H$ radiation results in a radiation with an effective wavelength of $\lambda_R$ corresponding to an attenuation coefficient $\mu_{R\text{-}background}$ that equals the attenuation coefficient $\mu_{P\text{-}background}$ for the background portion of sample 10. Measurements are then taken, during which the optically combined $\lambda_L$ and $\lambda_H$ radiations (i.e., the $\lambda_R$ radiation) are directed at sample 10 and the transmitted portion of the combined $\lambda_L$ and $\lambda_H$ radiations (i.e., the $\lambda_R$ radiation) are measured.

Alternative embodiments, in which a numerical (as opposed to optical) balancing process is performed after the acquisition of measurements (instead of before the acquisition of measurements or in addition to some optical balancing performed before the acquisition of measurements), are described below. In these embodiments, such balancing may be performed numerically on data that results from the acquisition of measurements. In some embodiments, the measurements may be performed with reference and principal radiations that have not been, prior to data acquisition part of the measurement, optically balanced at all, or that have been fully or approximately optically balanced. For purposes of this disclosure, methods that include numerical balancing after measurements are obtained, without a need for modifications to the light sources' wavelengths or output powers during the measurement, regardless if prior optical balancing was performed or not, are referred to as Post-Balancing. In one embodiment of the present invention, the optical powers of the light sources and signal gains are adjusted in the beginning of the measurement to ensure that the signal detector 22 is not saturated with excess radiation. The initial part of the measurement that deals with intensity and gain adjustments, hardware calibrations, etc., is not presented in FIG. 2 and FIG. 4 and is not discussed in this document.

Figure 2:
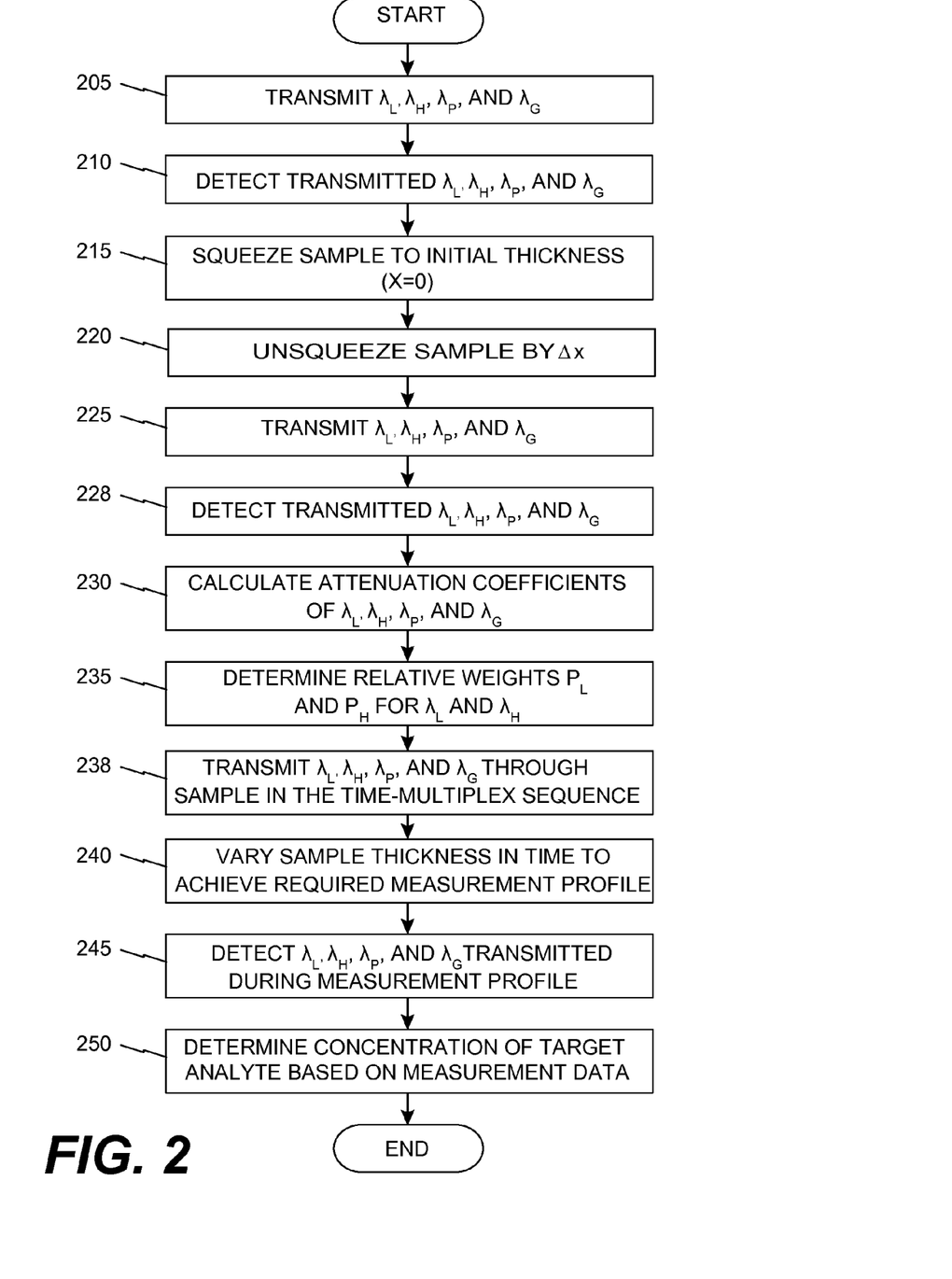
FIG. 2 depicts an exemplary noninvasive method of measuring a concentration of an analyte in a sample.

FIG. 2 depicts an exemplary method 300 according to an embodiment by which measurement data are obtained. The method may be performed by controller 30, for example, by processor 32 executing instructions stored in storage 34 and/or memory 36. In one embodiment, a part or all of the processing of the measurement data can be done by custom designed components, for example, ASICs (application specific integrated circuits).

At step 205, controller 30 may transmit $\mu_L$, $\lambda_H$, $\lambda_P$ and $\lambda_G$ radiations through sample 10 utilizing light sources 12, 14, 16 and 17. In one embodiment, controller 30 may sequentially turn on light sources 12, 14, 16 and 17, so that radiations are transmitted through sample 10 one at a time.

At step 210, detector 22 may detect the respective intensities of the $\lambda_L$, $\lambda_H$, $\lambda_P$ and $\lambda_G$ radiations that are transmitted through sample 10. Controller 30 may convert the detected signals into measurement data.

At step 215, controller 30 may direct the sample content alteration device 18 to squeeze sample 10 from its original unaltered thickness to a predetermined initial thickness (or pressure). Sample thickness is represented by x, and the initial squeezed thickness is represented as x=0. At the initial thickness, sample 10 may be characterized as including only the sample background without any target analyte. In other words, the unavoidable amounts of target analyte and target analyte carrier that are present in the sample at the initial thickness are considered to be part of the background material. For example, an earlobe may be squeezed so that most of the blood in the earlobe is displaced and the amount of glucose at the measurement site of sample 10 is reduced.

In another exemplary embodiment, at step 215, controller 30 may direct the sample content alteration device 18 to in a time-wise or spatial way modify an amount of a sample 10 component to achieve a certain condition. For example, squeeze sample 10 till the green light level (inversely proportional to the amount of blood at the measurement site) reaches a preset value (equal to most of the blood being squeezed out of the measurement site).

At the end of step 215, controller may detect the respective intensities of the $\lambda_L$, $\lambda_H$, $\lambda_P$ and $\lambda_G$ radiations that are transmitted through sample 10, utilizing signal detector 22. The detected transmitted intensities for $\lambda_L$, $\lambda_H$, Hp and $\lambda_G$ are represented as data points DCSP(0), DCSRL(0), DCSRH(0), and GREEN(0), respectively. "(0)" indicates reading at time=0.

At step 220, controller 30 may, after a brief delay to allow the tissue to stabilize at the set state (thickness or pressure), unsqueeze sample 10 by a small predetermined amount $\Delta x$. $\Delta x$ may be chosen in such a way that the thickness of the sample background in sample 10 increases, but the concentration of target analyte within sample 10 remains the same—there is no major influx of blood into the sample.

In another exemplary embodiment, at step 220, controller 30 may direct the sample content alteration device 18 to in a time-wise or spatial way modify an amount of a sample 10 component to achieve a certain condition. For example, unsqueeze sample 10 till the green light level (inversely proportional to the amount of blood at the measurement site) starts decreasing fast (indicating a blood influx into the measurement site).

At step 225, controller 30 may transmit radiation of wavelength $\lambda_L$, $\lambda_H$, $\lambda_P$ and $\lambda_G$ through sample 10 at the new thickness $\Delta x$. In one embodiment, controller 30 may sequentially turn on light sources 12, 14, 16 and 17, so that radiations are transmitted through sample 10 one at a time.

At step 228, controller may detect the respective intensities of the $\lambda_L$, $\lambda_H$, $\lambda_P$ and $\lambda_G$ radiations that are transmitted through sample 10 at the new thickness $\Delta x$, utilizing signal detector 22. The reading number (in a data array sequence, typically called "sample number") corresponding to sample thickness increase from x=0 by $\Delta x$ is T1. The amount of transmitted light is represented by DCSP(T1), DCSRL(T1), DCSRH(T1), and GREEN(T1), respectively. Note: DCSP, DCSRL, DCSRH and GREEN are data arrays, and, for example, DCSP(T1) is one element of the DCSP array, that was acquired at time=T1 when x=$\Delta x$.

At step 230, controller 30 may calculate the attenuation coefficients $\mu_{L\text{-}background}$, $\mu_{H\text{-}background}$, $\mu_{P\text{-}background}$ and $\mu_{G\text{-}background}$ of the sample background at $\lambda_L$, $\lambda_H$, $\lambda_P$ and $\lambda_G$ respectively. In one exemplary embodiment, the calculation of the attenuation coefficients is based on the change in the amount of light that is transmitted by the sample when squeezed at the initial thickness x=0 and squeezed at the new thickness x=$\Delta x$. Specifically, controller 30 may calculate each attenuation coefficient based on Eq. 1, where Signal stands for DCSP, RDCRL, DCSRH or GREEN.

$$\mu_{\lambda\text{-}background} = -\frac{1}{\Delta x} \cdot \log \frac{\text{Signal}(T1)}{\text{Signal}(0)} \qquad \text{Eq. 1}$$

In one exemplary embodiment, controller may measure DCSP(0), DCSRL(0), DCSRH(0), GREEN(0), DCSP(T1), DCSRL(T1), DCSRH(T1) and GREEN(T1) in one squeeze-unsqueeze cycle, as described above with respect to steps 205 to 228. In another exemplary embodiment, controller may measure DCSP(0) and DCSP(T1), DCSRL(0) and DCSRL(T1), DCSRH(0) and DCSRH(T1) and/or GREEN (0) and GREEN(T1) in two or more separate squeeze and unsqueeze cycles. For example, controller 30 may perform steps 205 to 228, but transmit and detect only $\lambda_L$. Controller 30 may then repeat steps 205 to 228, but transmit and detect only $\lambda_H$. Controller 30 may then again repeat steps 205 to 228, but transmit and detect only $\lambda_P$.

In another exemplary embodiment, controller may measure DCSP(i), DCSRL(i), DCSRH(i) and GREEN(i) continuously (from, for example, i=0 to i=T1) during a squeezing and/or unsqueezing cycle, and use that data for the calculation of the attenuation coefficients.

At step 235, controller 30 may determine relative weights $P_L$ and $P_H$ for $\lambda_L$ and $\lambda_H$ based on $\mu_{L\text{-}background}$, $\mu_{H\text{-}background}$, and $\mu_{P\text{-}background}$ calculated at step 230, using Eq. 2.

$$P_H = \frac{\mu_{P\text{-}background} - \mu_{L\text{-}background}}{\mu_{H\text{-}background} - \mu_{L\text{-}background}} \quad P_L = 1 - P_H \qquad \text{Eq. 2}$$

$$\lambda_R = P_L \cdot \lambda_L + P_H \cdot \lambda_H \qquad \text{Eq. 2a}$$

$$\mu_{R\text{-}background} = P_H \cdot \mu_{H\text{-}background} - P_L \cdot \mu_{L\text{-}background} \qquad \text{Eq. 3}$$

Eq. 2 determines relative weights $P_L$ and $P_H$ for $\lambda_L$ and $\lambda_H$ radiations so that if the $\lambda_L$ radiation and the $\lambda_H$ radiation were physically combined at these weights, the resulting radiation would have an attenuation coefficient $\mu_{R\text{-}background}$ that is the best fit to the attenuation coefficient $\mu_{P\text{-}background}$ obtained at step 230.

Figure 3:
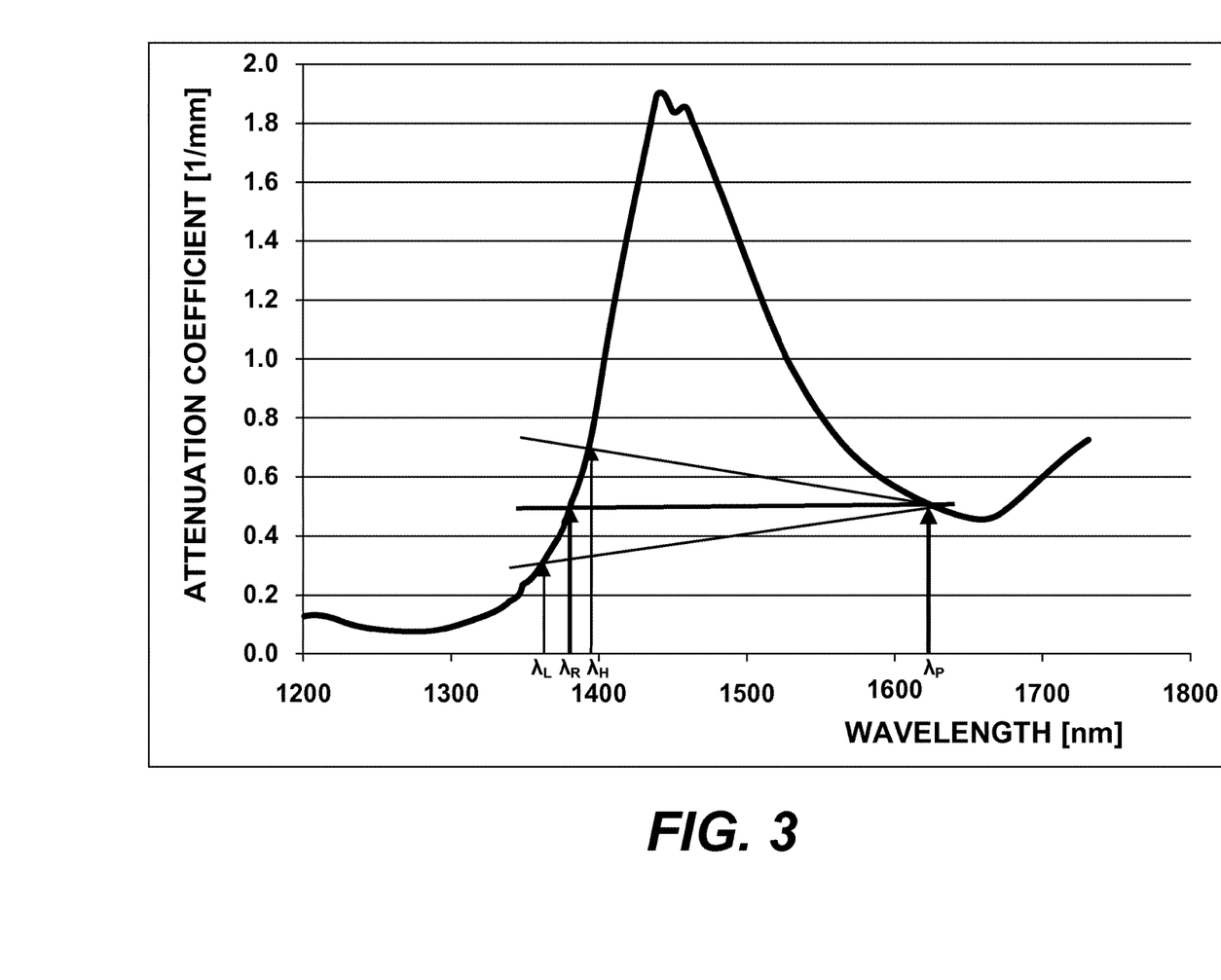
FIG. 3 depicts an exemplary attenuation spectrum of a sample.

Eq. 2 assumes that $\lambda_L$ and $\lambda_H$ and therefore $\mu_{L\text{-}background}$, $\Xi_{R\text{-}background}$, $\mu_{H\text{-}background}$ are on a portion of the attenuation spectrum of the sample background that can be approximated to be linear. FIG. 3 illustrates an exemplary attenuation spectrum in the near infrared range for a water dominant sample background like human earlobe tissue. The attenuation spectrum depicts the attenuation coefficient $\mu$ of the sample background versus the wavelength $\lambda$ of the attenuated radiation. In one example, principal wavelength $\lambda_P$ may be set at about 1630 nm on the right hand side of the attenuation peak, which corresponds to an attenuation coefficient $\mu_{P\text{-}background}$ of about 0.485/mm. Also, $\lambda_L$=1375 nm ($\mu_{L\text{-}background}$=0.430/mm) and $\lambda_H$=1385 nm ($\mu_{H\text{-}background}$=0.567/mm) (e.g. laser diodes 12 and 14 are configured to emit 1375 nm and 1385 nm respectively), as depicted in FIG. 3 (Note: In order to improve visualization, in FIG. 3, $\lambda_L$ and $\lambda_H$ were not drawn at 1375 nm and 1385 nm, so their attenuation coefficients do not correspond to the values presented in the text). Using Eq. 2 it can be calculated that weights $P_L$=0.6 and $P_H$=0.4 for the combination of the given $\lambda_L$ and $\lambda_H$ radiations, would result in a combined reference radiation with an effective wavelength of 1379 nm and a corresponding attenuation coefficient $\mu_{R\text{-}background}$ of 0.485/mm that matches the attenuation coefficient at the principal wavelength $\lambda_P$. By varying the relative weights corresponding to $\lambda_L$ and $\lambda_H$ radiations, the attenuation coefficient $\mu_{R\text{-}background}$ of the combined reference radiations can be arbitrarily tuned to any value between $\mu_{L\text{-}background}$ and $\mu_{H\text{-}background}$, based on Eq. 2.

In contrast to some embodiments (such as those that utilize only optical OPTICAL BRIDGE™ balancing methods OOBB, as described in, for example, U.S. patent No. '666), in which after step 235, laser diodes 12 and 14 would be operated to simultaneously direct their reference radiations at sample 10 at relative powers (calculated based on, for example, Eq. 2) and their transmitted portions through sample 10 would be measured as one combined signal, at step 240 of FIG. 2, controller 30 may operate diode laser 12 and diode laser 14 to be turned on at separate times. In addition, controller 30 may also operate diode laser 17 (corresponding to $\lambda_P$) and LED 18 (corresponding to $\lambda_G$) each to be on at separate times. In such embodiment, $\lambda_L$, $\lambda_H$, $\lambda_P$, and/or $\lambda_G$ radiations are not physically combined. Particularly, $\lambda_L$ and $\lambda_H$ radiations are not physically (nor optically) combined.

In an exemplary embodiment of steps 238 and 240, controller 30 may operate light sources 12, 14, 16, and 17 so that a time-multiplexed radiation with a repeating sequence of $\lambda_L$, $\lambda_H$, $\lambda_P$, and $\lambda_G$ radiations is emitted onto sample 10. In an exemplary embodiment, this time-multiplexed radiation may be transmitted through sample 10 during a measurement sequence executed by controller 30. For example, a measurement sequence may include controller 30 to command device 18 to change the thickness of sample 10 to various values, according to a measurement plan (as, for example, in FIG. 4).

At step 245, controller 30 may detect the transmitted intensities of the time-multiplexed radiations through sample 10 by utilizing sample detector 22 and generate separate measurement data corresponding to each of the $\lambda_L$, $\lambda_H$, $\lambda_P$, and/or $\lambda_G$ radiations. The amount of each radiation that is transmitted through sample 10 depends on the attenuation coefficients of the sample background, the target analyte carrier and the target analyte at these wavelengths, and the amount of the sample background, target analyte carrier and the target analyte present in sample 10.

Figure 4:
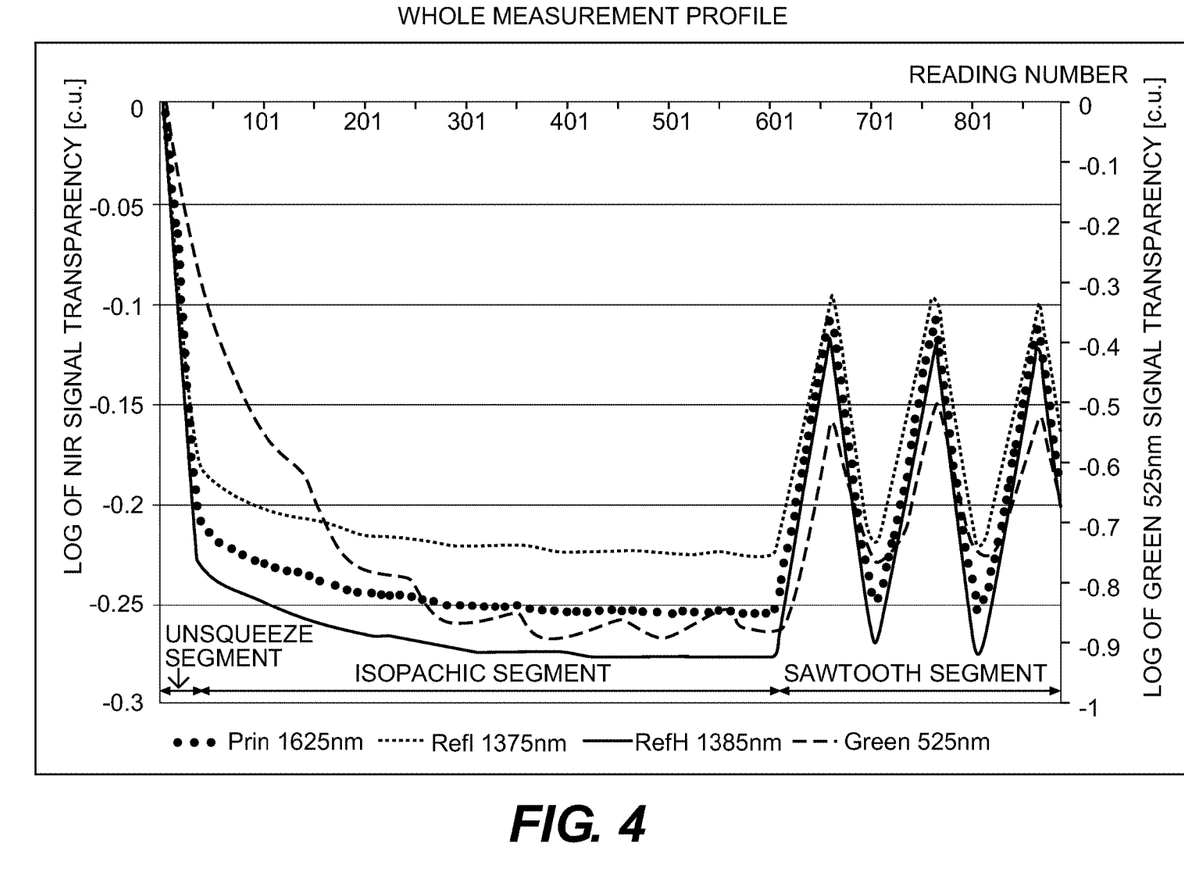
FIG. 4 depicts exemplary measurement data for determining the concentration of an analyte in a sample.

FIG. 4 depicts a graph of an exemplary set of measurement data obtained at step 245, during an exemplary measurement sequence off a human ear. The graph includes four measurement curves corresponding to detected intensities of radiations of wavelengths $\lambda_L$, $\lambda_H$, $\lambda_P$, and $\lambda_G$. Each data point represents a reading of a detected intensity from sample detector 22. One reading at each wavelength $\lambda_L$, $\lambda_H$, $\lambda_P$, and $\lambda_G$ is made each 10 ms-100 readings are collected per second per wavelength.

In one embodiment, as shown in FIG. 4, the measurement sequence may begin with sample 10 in a squeezed state (utilizing sample thickness alteration device 18) in which we assume that sample 10 contains only background. Then, an Unsqueeze may occur, in which sample 10 is unsqueezed (in FIG. 4, the first 33 readings/data points), causing a fast increase in the thickness of the background and blood content of sample 10. The measured intensities of $\lambda_L$, $\lambda_H$, $\lambda_P$, and $\lambda_G$ radiations that are transmitted through sample 10 decrease as a result of the increase in the thickness of sample background and blood, along with the glucose that is carried in by the influx of blood into the measurement site of sample 10. The measurement may also include an Isopachic (constant thickness) Segment, during which the influx of blood continues into sample 10 in an exponential decay manner filling sample 10 and displacing the background tissue (mostly visible in the Green signal in FIG. 4). The total thickness of sample 10 on the Isopachic Segment may be kept constant (In FIG. 4, the Isopachic Segment lasts from data point 34 till data point 620). On this segment, a pulsation (due to heart beats) of the blood in the unsqueezed sample can be extracted from the measurement. Finally, a SawTooth Segment may follow (data points 621-900), during which the thickness of sample 10 is altered in a sawtooth patter by using the sample thickness alteration device 18. The SawTooth may be synchronized with the heart pulsation: squeezes may occur during diastole, and unsqueezes may occur during systole. Non-synchronized SawTooth produces preset sample thickness variations.

With reference back to FIG. 2, at step 250, controller 30 may determine the concentration of the target analyte based on the measurement curves corresponding to $\lambda_L$, $\lambda_H$, $\lambda_P$, and $\lambda_G$. In one example, if relative weights $P_L$ and $P_H$ are calculated according to Eq. 2, controller 30 could sum the measurement data corresponding to $\lambda_L$ and $\lambda_H$ to generate a Combined Bridge Signal array that would be equivalent to the difference between the $\lambda_P$ measurement curve and measurement curve obtained from the transmission of an OPTICAL BRIDGE™ balanced $\lambda_R$ radiation (the numerical combination of OPTICAL BRIDGE™ balanced $\lambda_L$ and $\lambda_H$ radiations—see Eq. 2) through sample 10—see Eq. 4.

Combined Bridge Signal(i)=DCSP(i)−($P_L$·DCSRL(i)+ $P_H$·DCSRH(i))    Eq. 4

In another embodiment, controller 30 may, instead of, or in addition to, performing steps 220-235, perform additional computational processing at step 250 on the measurement data obtained at step 245, to determine new weights for summing $\lambda_L$ and $\lambda_H$ measurement data into the Combined Bridge Signal (see Eq. 4). I.e., controller 30 may perform numerical Post-Balancing without specifically dedicated balancing measurement steps (like steps 220-230 in FIG. 2), but solely by processing the measurement data obtained at steps 238-245. We will call this option Continuous Post-Balancing—CPB while the Post-Balancing that requires a thickness variation step (like step 220 in FIG. 2) we will refer to as Step Based Post-Balancing—or SBPB. Embodiments for CPB are described in further detail below. Since CPB is performed on the measurement data, and not prior to the measurement, it may result in being able to make more accurate determinations of the target analyte concentration as compared with using an OOBB $\lambda_R$ signal as described in previous disclosures, such as the '666 patent, or SBPB using steps 220-230 in FIG. 3.

SBPB or CPB balancing methods may result in a more accurate determination of the target analyte concentration compared to OOBB when the relative powers that diode lasers 12 and 14 would need to be operated at, to achieve an optically balanced reference wavelength $\lambda_R$, are significantly unequal. The reasoning follows: For optical balancing OOBB, the laser powers are kept at levels needed to achieve balancing. In some exemplary situations, when the desired $\lambda_R$ (see Eq. 2) is approximately near the center between $\lambda_L$ and $\lambda_H$, the relative powers of diode lasers 12 and 14 may be 0.5:0.5, and therefore both may be operated at 80-90% of their full power. This operational configuration is good. However, when the desired $\lambda_R$ is close to one of $\lambda_L$ or $\lambda_H$, the relative powers of diode lasers 12 and 14 may be more unequal, e.g., 0.2:0.8, in which case one of the diode lasers may need to be operated at very low (~15%) power. Operation at low power may produce laser instabilities and excessive noise in the measurement signal, leading to inaccurate estimates of the target analyte concentration.

Post-Balancing allows the acquisition of measurements with diode lasers operating at their optimal powers (80-90% full power) because the laser intensities are set prior to balancing. Therefore, the measurement signals and data are acquired with low laser noise and under most stabile laser operating conditions. With Post-Balancing, the $\lambda_L$ and $\lambda_H$ radiations are transmitted independently through sample 10, and independent measurement data corresponding to $\lambda_L$ and $\lambda_H$ are obtained. Therefore, controller 30 can numerically perform a weighted summation of the $\lambda_L$ and $\lambda_H$ measurement data so that the $\lambda_{L+H}$ data is balanced with the $\lambda_P$ data within the Combined Bridge Signal, with respect to the sample background. So, if the balancing weights are calculated to be, for example, 0.2:0.8, all laser powers will still be 80-90% full power, however, controller 30 will computationally perform a weighted summation of 0.2 of the $\lambda_L$ measurement data and 0.8 of the $\lambda_H$ measurement data.

An exemplary reason why CPB might be selected instead of optical OPTICAL BRIDGE™ balancing OOBB or even SBPB is that in order to perform OOBB or SBPB, it is indicated to first squeeze the sample and then unsqueeze it by $\Delta x$. It has been demonstrated that the calculated attenuation coefficients $\mu_{P\text{-}background}$, $\mu_{L\text{-}background}$, $\mu_{H\text{-}background}$, and $\mu_{G\text{-}background}$ using OOBB or SBPB may depend upon the selected initial pressure (for x=0) or initial thickness of sample 10—step 215 in FIG. 2. There may not be one singular thickness or pressure at which sample 10 must be squeezed to so that there is no target analyte present within it, but rather a range of thicknesses and/or pressures in which this condition is met to a varying degree. This may be due to the fact that at different initial pressures/thicknesses, the sample 10 content might be different (e.g., different amount of fat, blood and glucose). Therefore, at different initial conditions, we have a different sample background. Of the various values of reference wavelength $\lambda_R$ (see Eq. 2a) that can result from different initial conditions, there may be a relatively optimal $\lambda_R$ for calculating the most accurate obtainable estimate of the target analyte concentration. However, it may not be clear which of these different initial pressures/thicknesses may provide the relatively optimal $\lambda_R$. Furthermore, some samples, such as biological samples, are dynamic and composed of constantly changing components. The relatively optimal $\lambda_R$ and corresponding thickness may vary for measurements taken at different times for the same sample, vary from sample to sample, or even vary within one measurement for a single sample. Given the variability, there is currently no method for predetermining the correlative initial squeeze pressure/thickness that results in obtaining the relatively optimal effective reference wavelength $\lambda_R$ for a given measurement. Contrarily, CPB may be performed dynamically, and the background can be defined and measured for an unsqueezed tissue state, which is more consistent.

Another exemplary reason why CPB might be selected instead of optical OPTICAL BRIDGE™ balancing OOBB or even SBPB is that in order to perform OOBB or SBPB, we have to first squeeze the sample and then unsqueeze it by $\Delta x$. It has been demonstrated that the calculated attenuation coefficients $\mu_{P\text{-}background}$, $\mu_{L\text{-}background}$, $\mu_{H\text{-}background}$, and $\mu_{G\text{-}background}$ using OOBB or SBPB may depend upon the selected balancing step unsqueeze $\Delta x$ of sample 10—step 220 in FIG. 2. This may be due to the fact that at different balancing steps, the sample content might be different (e.g., more or less blood and glucose may come into the sample or different rearrangement of the tissue matrix in an earlobe sample). Therefore, at different balancing steps, we have a different sample background change. Of the various values of reference wavelength $\lambda_R$ (see Eq. 2a) that can result from different balancing steps $\Delta x$, there may be a relatively optimal $\lambda_R$ for calculating the most accurate estimate of the target analyte concentration. However, it may not be clear which of these different balancing steps may provide the relatively optimal $\lambda_R$. Furthermore, some samples, such as biological samples, are dynamic and composed of constantly changing components. The relatively optimal $\lambda_R$ and corresponding optimal balancing step sizes may vary for measurements taken at different times for the same sample, vary from sample to sample, or even vary within one measurement for a single sample. Given the variability, there is currently no method for predetermining the correlative balancing step size that results in obtaining the relatively optimal effective reference wavelength $\lambda_R$ for a given measurement. Contrarily, CPB is performed on data segments with continuously varying sample thicknesses (Unsqueeze and/or SawTooth Segments), and constant sample thickness (Isopachic Segment), and the background attenuation coefficients can be defined and measured in a more consistent way.

As discussed above, controller 30 may perform additional computational processing in step 245 of FIG. 2, to determine weights for a weighted summation of the $\lambda_L$ signal and the $\lambda_H$ signal to obtain a virtually synthesized, combined reference $\lambda_R=\lambda_{L+H}$ signal that balances the $\lambda_P$ signal, and the Combined Bridge Signal, in the process called Continuous Post-Balancing—CPB. The calculation of the weights, as presented in Eq. 2, is based on calculation of the background attenuation coefficients $\mu_{P\text{-}background}$, $\mu_{L\text{-}background}$, and $\mu_{H\text{-}background}$. A detailed description of one example by which the weights can be determined is now described. The explanation will assume a set of measurement data similar to that shown in FIG. 4. We will maintain the same nomenclature for the signals as in the previous text, except that since we are here explicitly dealing with arrays of data, we will use standard Matlab notation for data arrays: DCSP(i), DCSRL(i), DCSRH(i) and GREEN(i), where "i" represents the reading or data point number.

For example, first, we can define three signal slopes that can be calculated on the Isopachic Segment (where sample 10 thickness is constant): PRINSlope, REFLSlope and REFHSlope—see Eqs, 5a, 5b, and 5c. Basically, these slopes represent the sensitivities of the near-infrared attenuations vs. sensitivity of the green attenuation to the blood (with glucose) influx and background tissue efflux from sample 10 on the Isopachic Segment. Controller 30 may calculate the actual values of these slopes according to Eqs. 6a, 6b and 6c. They represent least-square best fit equations. For the data acquired with a measurement process that yielded signals from FIG. 4, the summation limit EUS=34 (end of unsqueeze), while STStart=621 (SawTooth start).

Next, for example, we can define four signal slopes that can be calculated on the SawTooth Segment (where sample 10 thickness is varied): PSTSlope, RLSTSlope, RHSTSlope, and GSTSlope—see Eqs. 7a, 7b, 7c and 7d. Basically, these slopes represent the sensitivities of the near-infrared and green attenuations vs. sample thickness variation that include blood (with glucose) and background tissue influx and efflux from sample 10 on the SawTooth Segment. Controller 30 may calculate the actual values of these slopes according to Eqs. 8a, 8b, 8c and 8d. They represent least-square best fit equations. For the data acquired with a measurement process that yielded signals from FIG. 4, the summation limit STEnd=900 (end of SawTooth Segment), while STStart=621 (SawTooth start).

The recorded signals, presented in FIG. 4 are so called composite signals that include both decay (due to refilling of the capillary bed and small veins of sample 10) and pulsations (due to pulsatile blood movements in small arteries of sample 10). On the Isopachic Segment the recorded composite signal may be split up into decay-only and pulsation-only signals. In one embodiment, controller 30 may calculate the Isopachic Segment slopes according to Eqs. 5a, 6b and 6e using the decay-only signals.

In another embodiment, controller 30 may calculate the Isopachic Segment slopes according to Eqs. 65, 6b and 6c using the pulsation-only signals.

In another embodiment, controller 30 may calculate two sets of Isopachic Segment slopes according to Eqs. 6a, 6b and 6e using the pulsation-only signals (e.g. PRINSlope_Pulse) and the decay-only signals (e.g. PRINSlope_Decay). Controller 30 may calculate a weighted average of the pulsation-only Isopachic Segment slopes and the decay-only Isopachic Segment slopes to generate the final set of Isopachic Segment slopes. The Decay_Weight and Pulse_Weight may be, for example, calculated based on the contribution of each signal component to the composite signal. For example:

Based on the slopes calculated with Eqs. 7a, 7b, 7c, 8a, 8b, 8c and 8d (or Eq. 9), controller 30 may calculate the attenuation coefficients for the sample background for $\lambda_L$, $\lambda_H$, and $\lambda_P$ using Eqs. 10a, 10b, and 10c.

To achieve balancing with respect to the sample background, $\mu_{L+H\text{-}background}$ should equal $\mu_{P\text{-}background}$, so controller 30 may, according to Eq. 2, calculate the $P_L$ and $P_H$, which are the balancing weights for $\lambda_L$ and $\lambda_H$.

Controller 30 may, according to Eq. 4, generate the Combined Bridge Signal. This signal has a decreased background attenuation component, therefore, it can be used to calculate the estimate of glucose concentration in the blood.

The above example of computationally Post-Balancing the two reference signals With the principal signal is exemplary only. Other balancing rules, equations, and algorithms may be used to re-balance and re-process the data, sometimes over and over. For example, a more sophisticated, computational, iterative analysis may be performed using Post-Balancing.

Exemplary benefits of Post-Balancing are as follows. Post-Balancing may allow for measurement acquisition with lasers (or other radiation sources) that are all the time operating at their best operation regions with, for example, lowest noise. In addition, Post-Balancing may be performed on measurement data that is used for the analyte concentration estimation, instead of data that relates to the state of the sample prior to the measurement; this may allow for more accurate estimates. Furthermore, by varying the specific balancing algorithms used, it may be possible to re-balance and re-process the data for more fine-tuned, accurate estimates. Post-Balancing may also provide the ability to dynamically adjust the balancing process to specific samples.

It will be apparent to those skilled in the art that various modifications and variations can be made to the disclosed analyte measurement system. Other embodiments will be apparent to those skilled in the art from consideration of the specification and practice of the disclosed analyte measurement system. For example, in an exemplary embodiment of method 300, instead of modulating the sample thickness/pressure in a way that results in signals presented in FIG. 4, the sample thickness/pressure modulation might be periodic, sinusoidal, slower or faster than in the example, or there might be no external modulation at all, so the measurement relies on the blood pulsation pressure modulating the amount of the target analyte in the sample. As another example, determining relative weights $P_L$ and $P_H$ based on processing of the measurement data may be based on applying Eq. 6 to composite signals (that contain both decay and pulsation components, like the ones in FIG. 4) decay-only components of the acquired signals, pulsation-only components, or their weighted sums. Furthermore one or more components of the analyte measurement device may be omitted or arranged in different relations relative to each other than as disclosed. Also, in some embodiments, one or more disclosed steps may be omitted and or performed in different order than as described. Disclosed steps may be performed in parallel and/or serially. It is intended that the specification and examples be considered as exemplary only, with a true scope being indicated by the following claims and their equivalents.

$$PRINSlope(i) = \frac{\delta DCSP(i)}{\delta GREEN(i)}\bigg|_{Isopachic\ Segment} \quad \text{Eq. 5a}$$

$$REFLSlope(i) = \frac{\delta DCSRL(i)}{\delta GREEN(i)}\bigg|_{Isopachic\ Segment} \quad \text{Eq. 5b}$$

$$REFHSlope(i) = \frac{\delta DCSRH(i)}{\delta GREEN(i)}\bigg|_{Isopachic\ Segment} \quad \text{Eq. 5c}$$

$$PRINSlope = \frac{\sum_{i=EUS}^{STStart}\{DCSP(i)^2\}}{\sum_{i=EUS}^{STStart}\{GREEN(i)\cdot DCSP(i)\}}\bigg|_{Isopachic\ Segment} \quad \text{Eq. 6a}$$

$$REFLSlope = \frac{\sum_{i=EUS}^{STStart}\{DCSRL(i)^2\}}{\sum_{i=EUS}^{STStart}\{GREEN(i)\cdot DCSRL(i)\}}\bigg|_{Isopachic\ Segment} \quad \text{Eq. 6b}$$

$$REFHSlope = \frac{\sum_{i=EUS}^{STStart}\{DCSRH(i)^2\}}{\sum_{i=EUS}^{STStart}\{GREEN(i)\cdot DCSRH(i)\}}\Bigg|_{Isopachic\ Segment} \quad \text{Eq. 6c}$$

$$PSTSlope(i) = \frac{\delta DCSP(i)}{\delta Thickness(i)}\Bigg|_{SawTooth\ Segment} \quad \text{Eq. 7a}$$

$$RLSTSlope(i) = \frac{\delta DCSRL(i)}{\delta Thickness(i)}\Bigg|_{SawTooth\ Segment} \quad \text{Eq. 7b}$$

$$RHSTSlope(i) = \frac{\delta DCSRH(i)}{\delta Thickness(i)}\Bigg|_{SawTooth\ Segment} \quad \text{Eq. 7c}$$

$$GSTSlope(i) = \frac{\delta GREEN(i)}{\delta Thickness(i)}\Bigg|_{SawTooth\ Segment} \quad \text{Eq. 7d}$$

$$PSTSlope = \frac{\sum_{i=ST\,Start}^{STEnd}\{DCSP(i)^2\}}{\sum_{i=ST\,Start}^{STEnd}\{Thickness(i)\cdot DCSP(i)\}}\Bigg|_{SawTooth\ Segment} \quad \text{Eq. 8a}$$

$$RLSTSlope = \frac{\sum_{i=ST\,Start}^{STEnd}\{DCSRL(i)^2\}}{\sum_{i=ST\,Start}^{STEnd}\{Thickness(i)\cdot DCSRL(i)\}}\Bigg|_{SawTooth\ Segment} \quad \text{Eq. 8b}$$

$$RHSTSlope = \frac{\sum_{i=ST\,Start}^{STEnd}\{DCSRH(i)^2\}}{\sum_{i=ST\,Start}^{STEnd}\{Thickness(i)\cdot DCSRH(i)\}}\Bigg|_{SawTooth\ Segment} \quad \text{Eq. 8c}$$

$$GSTSlope = \frac{\sum_{i=ST\,Start}^{STEnd}\{GREEN(i)^2\}}{\sum_{i=ST\,Start}^{STEnd}\{Thickness(i)\cdot\{GREEN(i)\}\}}\Bigg|_{SawTooth\ Segment} \quad \text{Eq. 8d}$$

$$PRINSlope = \frac{PRINSlope\_Decay\cdot Decay\_Weight + PRINSlope\_Pulse\cdot Pulse\_Weight}{Decay\_Weight + Pulse\_Weight} \quad \text{Eq. 9}$$

$$\mu_{P-background} = GSTSlope\cdot PRINSlope - PSTSlope \quad \text{Eq. 10a}$$

$$\mu_{L-background} = GSTSlope\cdot REFLSlope - RLSTSlope \quad \text{Eq. 10b}$$

$$\mu_{H-background} = GSTSlope\cdot REFHSlope - RHSTSlope \quad \text{Eq. 10c}$$

The invention claimed is:

1. A noninvasive method for estimating a concentration of a target analyte in a sample, comprising:
   a.) generating a first reference radiation having a first reference wavelength, a second reference radiation having a second reference wavelength, a principal radiation having a principal wavelength, and a target analyte carrier detection radiation having the target analyte carrier detection wavelength, using a first reference light source, a second reference light source, a principal light source, and a target analyte carrier detection light source, respectively;
   b.) directing the first reference radiation, the second reference radiation, the principal radiation and the target analyte carrier detection radiation at the sample which includes the target analyte;
   c.) detecting, with one or more detectors, a first amount of the first reference radiation, a second amount of the second reference radiation, a third amount of the principal radiation, and a fourth amount of the target analyte carrier detection radiation, that leaves the sample;
   d.) causing or permitting modulation of the content of the target analyte in the sample during the detecting step;
   e.) generating first reference measurement data, second reference measurement data, principal measurement data, and target analyte carrier detection measurement data, based respectively on the first amount, the second amount, the third amount, and the fourth amount of radiation that are detected;
   f.) calculating balancing weights for a weighted combination of the first reference measurement data and the second reference measurement data that balances the principal measurement data with respect to a sample background from the first reference measurement data, the second reference measurement data, and the principal measurement data, using one or more processors; and
   g.) estimating the concentration of the target analyte based on the difference between the balanced weighted combination of the first reference measurement data and the second reference measurement data and the principal measurement data, and the target analyte carrier detection data using subsequent measurement data.

2. The method of claim 1, wherein:
the first reference radiation, the second reference radiation, the principal radiation, and the target analyte carrier detection radiation are directed at the sample in a repeating, time-multiplexed sequence.

3. The method of claim 1, wherein:
the sample is adjusted to a plurality of thicknesses while the first reference radiation, the second reference radiation, the principal radiation, and the target analyte carrier radiation are directed at the sample and the first amount, the second amount, the principal amount, and the target analyte carrier amount are detected.

4. The method of claim 3, wherein the target analyte is blood glucose and the target analyte carrier is blood.

5. The method of claim 3, wherein the target analyte is interstitial glucose and the target analyte carrier is interstitial fluid.

6. The method of claim 3, wherein the target analyte is a blood analyte and the target analyte carrier is blood.

7. The method of claim 3, wherein the target analyte is an interstitial analyte and the target analyte carrier is interstitial fluid.

8. The method of claim 1, wherein:
the first amount, the second amount, the third amount and the fourth amount of radiation that leave the sample are portions of the first reference radiation, the second reference radiation, the principal radiation and the target analyte carrier detection radiation that are transmitted through the sample.

9. The method of claim 1, wherein:
the first amount, the second amount, the third amount and the fourth amount of radiation that leave the sample are portions of the first reference radiation, the second reference radiation, the principal radiation, and the target analyte carrier detection radiation that are transflected by the sample.

10. The method of claim 1, wherein:
the step of calculating balancing weights involves determining the relative balancing weights of the first reference radiation and the second reference radiation that are needed to produce a weighted combination of the first reference measurement data and the second reference measurement data with the principal measurement data, in such a manner that the weighted combination values are not influenced by the variations of the thicknesses of those
compartments of the sample that do not contain the target analyte or the target analyte carrier.

11. The method of claim 10: comprising:
balancing an Optical Bridge, using measurement data detected from a sample that is made up of mostly background material, with only minimal amounts of target analyte carrier and target analyte.

12. The method of claim 11, wherein:
the relative preliminary balancing weights are determined by:
comparing an amount of the first reference radiation that leaves the sample when in a first state with an amount of the first reference radiation that leaves the sample in a second state to determine a first reference attenuation coefficient of the sample background at the first reference wavelength;
comparing an amount of the second reference radiation that leaves the sample when in a first state with an amount of the second reference radiation that leaves the sample in a second state to determine a second reference attenuation coefficient of the sample background at the second reference wavelength;
comparing an amount of the principal radiation that leaves the sample when in a first state with an amount of the principal radiation that leaves the sample in a second state to determine a principal attenuation coefficient of the sample background at the principal wavelength; and
determining relative preliminary balancing weights such that the first reference attenuation coefficient of the sample background and
the second reference attenuation coefficient of the sample background, when combined, equals the principal attenuation coefficient of the sample background.

13. The method of claim 12, wherein:
the first state and the second state correspond to different sample thicknesses.

14. The method of claim 13, wherein:
the first states of the sample for determining the first reference attenuation coefficient, the second reference attenuation coefficient and the principal attenuation coefficient respectively correspond to sample thicknesses that are substantially the same; and
the second states of the sample for determining the first reference attenuation coefficient, the second reference attenuation coefficient, and the principal attenuation coefficient respectively correspond to sample thicknesses that are substantially the same.

15. The method of claim 13, wherein:
the first state of the sample for determining the first reference attenuation coefficient, the second reference attenuation coefficient, and the principal attenuation coefficient respectively correspond to thicknesses of the sample that are different; and
the second states of the sample for determining the first reference attenuation coefficient, the second reference attenuation coefficient, and the principal attenuation coefficient, respectively correspond to thicknesses of the sample that are different.

16. The method of claim 13, wherein:
the sample thicknesses that correspond to the states of the sample are dynamically chosen during the measurement, based on the first amount, the second amount, the third amount, the fourth amount of radiation that leaves the sample and the pressure measured on the sample.

17. The method of claim 12, wherein:
the first state corresponds to a thickness of the sample when minimal amount of target analyte is present in the sample; and
the second state corresponds to a different thickness of the sample when also minimal amount of target analyte is present in the sample.

18. The method of claim 10, further comprising:
balancing an Optical Bridge, using the first reference measurement data, the second reference measurement data, the principal measurement data and the target analyte carrier detection measurement data, detected from a sample that has varying amounts of background material, target analyte and target analyte carrier.

19. The method of claim 1, wherein:
the first reference light source and the second reference light source are throughout the whole measurement operated, in a pulsed or continuous mode, at constant operation regions that correspond to the best light source stability and least amount of optical noise.

20. The method of claim 1, further comprising:
performing multiple iterations of processing the first reference measurement data, the second reference measurement data, the principal measurement data, and the target analyte detection measurement data, to improve on the accuracy of the calculated relative preliminary balancing weights and to produce the relative balancing weights that are best representative of the sample background.

21. The method of claim 10, wherein the modification comprises:
an Unsqueeze Segment during which the thickness of the sample is monotonously increased;
an Isopachic Segment, during which the thickness of the sample is held constant; and,
a SawTooth segment, during which the thickness of the sample is being varied in a predetermined manner.

22. The method of claim 21, wherein:
the relative balancing weights are determined by:
calculating a first reference sawtooth slope, defined as the first reference measurement data variation vs. sample thickness variation on the measurement segment on which the sample thickness is varied in the predetermined manner;
calculating a second reference sawtooth slope, defined as the second reference measurement data variation vs. sample thickness variation on the measurement segment on which the sample thickness is varied in the predetermined manner;
calculating a principal sawtooth slope, defined as the principal measurement data variation vs. sample thickness variation on the measurement segment on which the sample thickness is varied in the predetermined manner;
calculating a green sawtooth slope, defined as the target analyte carrier detection measurement data variation vs. sample thickness variation on the measurement segment on which the sample thickness is varied in the predetermined manner;
calculating the first reference slope, defined as the first reference measurement data variation vs. target analyte carrier detection measurement data variation on the measurement segment on which the sample thickness is constant;
calculating the second reference slope, defined as the second reference measurement data variation vs. target analyte carrier detection measurement data variation on the measurement segment on which the sample thickness is constant;

calculating the principal slope, defined as the principal measurement data variation vs. target analyte carrier detection measurement data variation on the measurement segment on which the sample thickness is constant;

determining a first reference attenuation coefficient of the sample background at the first reference wavelength based on the first reference sawtooth slope, the green sawtooth slope and the first reference slope;

determining a second reference attenuation coefficient of the sample background at the second reference wavelength based on the second reference sawtooth slope, the green sawtooth slope and the second reference slope;

determining a principal attenuation coefficient of the sample background at the principal wavelength based on the principal sawtooth slope, the green sawtooth slope and the principal slope;

determining the relative balancing weights such that the first reference attenuation coefficient of the sample background and the second reference attenuation coefficient of the sample background so that their combination equals the principal attenuation coefficient of the sample background, based on the first reference attenuation coefficient, the second reference attenuation coefficient and the principal attenuation coefficient.

23. An apparatus for performing noninvasive estimation of a concentration of a target analyte in a sample, comprising:
   a.) a first reference light source for generating a first reference radiation;
   b.) a second reference light source for generating a second reference radiation;
   c.) a principal light source for generating a principal radiation;
   d.) a target analyte carrier detection light source for generating a target analyte carrier detection radiation;
   e.) a device for altering the content of target analyte, target analyte carrier and sample background material within the sample;
   f.) one or more detectors for detecting non-optical sample parameters selected from the group consisting of sample thickness, pressure on the sample and temperature;
   g.) one or more detectors for detecting the first reference radiation, the second reference radiation, the principal radiation and the target analyte carrier detection radiation and generating the corresponding first measurement data, second measurement data, principal measurement data, and target analyte carrier detection data; and
   h.) a controller configured to estimate the concentration of the target analyte by:
   processing the first measurement data, second measurement data, principal measurement data, and target analyte carrier detection data, using one or more processors, to obtain the first reference attenuation coefficient, the second reference attenuation coefficient, the principal attenuation coefficient, and the target analyte carrier attenuation coefficient of the sample background;
   i.) processing the obtained first reference, second reference, principal, and target analyte carrier sample background attenuation coefficients to find the balancing weights needed to generate a weighted combination of the first reference measurement data and the second reference measurement data that balances the principal measurement data with respect to a sample background; and,
   j.) estimating, using subsequent measurement data and the target analyte carrier attenuation coefficient, the concentration of the target analyte based on the difference between the balanced weighted combination of the first reference measurement data and the second reference measurement data vs. the principal measurement data.

24. The apparatus of claim 23, wherein:
the controller is configured to operate the first reference light source, the second reference light source, the principal light source and the target analyte carrier detection light source to generate a repeating, time-multiplexed sequence of the first reference radiation, the second reference radiation, the principal radiation and the target analyte carrier detection radiation.

25. The apparatus of claim 23, wherein:
the controller is configured to control the device which alters the content of the target analyte, target analyte carrier and sample background material within the sample.

26. The apparatus of claim 23, wherein the target analyte is blood glucose and the target analyte carrier is blood.

27. The apparatus of claim 23, wherein the target analyte is interstitial glucose and the target analyte carrier is interstitial fluid.

28. The apparatus of claim 23, wherein the target analyte is a blood analyte and the target analyte carrier is blood.

29. The apparatus of claim 23, wherein the target analyte is an interstitial analyte and the target analyte carrier is interstitial fluid.

30. The apparatus of claim 23, wherein the measurements are performed on the target analyte carrier that is temporarily or permanently removed from the sample.

* * * * *